(12) United States Patent
Kwon et al.

(10) Patent No.: US 7,288,552 B2
(45) Date of Patent: Oct. 30, 2007

(54) PIPERIDINE DERIVATIVES, PROCESS FOR PREPARATION THEREOF, AND PHARMACEUTICAL COMPOSITION FOR ALZHEIMER'S DISEASE CONTAINING THE SAME

(75) Inventors: Young-Ee Kwon, Seoul (KR); Jeong-Ho Kang, Seoul (KR); Hwa-Jung Lee, Gurni-sil (KR); Sang-Jae Lee, Gimpo-si (KR); Do-Wan Kim, Seoul (KR); Kang-Hoon Lee, Siheung-si (KR); Sun-Il Han, Seoul (KR); You-Sun Yoon, Inchon-sll (KR)

(73) Assignee: STC NARA Co., Ltd., Chungcheongnam-do (KR)

( * ) Notice: Subject to any disclaimer, the term of this patent is extended or adjusted under 35 U.S.C. 154(b) by 520 days.

(21) Appl. No.: 10/492,984

(22) PCT Filed: Oct. 16, 2002

(86) PCT No.: PCT/KR02/01930

§ 371 (c)(1),
(2), (4) Date: Apr. 16, 2004

(87) PCT Pub. No.: WO03/033489

PCT Pub. Date: Apr. 24, 2003

(65) Prior Publication Data

US 2005/0043316 A1 Feb. 24, 2005

(30) Foreign Application Priority Data

Oct. 16, 2001 (KR) .................... 10-2001-0063778

(51) Int. Cl.
*A61K 31/445* (2006.01)
*A61K 31/455* (2006.01)
*C07D 211/46* (2006.01)

(52) U.S. Cl. ...................... 514/318; 514/327; 546/194; 546/221

(58) Field of Classification Search ................ 546/194, 546/221; 514/318, 327
See application file for complete search history.

(56) References Cited

U.S. PATENT DOCUMENTS

5,708,007 A * 1/1998 O'Malley et al. ........... 514/320

* cited by examiner

*Primary Examiner*—Bernard Dentz
(74) *Attorney, Agent, or Firm*—Nixon & Vanderhye P.C.

(57) ABSTRACT

The present invention relates to novel piperidine derivatives having effect of inhibiting acetylcholinesterase and aggregation of β-amyloid, Alzheimer's disease-induced protein, and treatment for Alzheimer's disease containing the same, the piperidine derivatives represented by Formula 3.

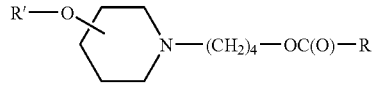

9 Claims, 3 Drawing Sheets

PIPERIDINE DERIVATIVES, PROCESS FOR PREPARATION THEREOF, AND PHARMACEUTICAL COMPOSITION FOR ALZHEIMER'S DISEASE CONTAINING THE SAME

This application is the US national phase of international application PCT/KR02/01930, filed in English on 16 Oct. 2002, which designated the US. PCT/KR02/01930 claims priority to KR Application No. 2001/63778 filed 16 Oct. 2001. The entire contents of these applications are incorporated herein by reference.

TECHNICAL FIELD

The present invention relates to novel piperidine derivatives and pharmaceutical compositions containing them. In particular, the present invention relates to novel piperidine derivatives useful for treating Alzheimer's disease and processes for preparing them.

BACKGROUND

As it becomes clear that $21^{st}$ century will be a silver society, people pursuit for high quality in life by having healthy and longer life without harmful diseases. Development in science increased the number of aged people to have longer life, and consequently it led to sudden increase rate in patients with Alzheimer's disease, which caused from neurological degeneration. Alzheimer's disease not only deteriorates the quality of personal and social life, but also puts the patients themselves and others in misery. Alzheimer's disease is the fourth highest death reason followed by cancer, heart disease, and cerebral apoplexy.

Studied statistics of the advanced countries show the percentage in number of patients with Alzheimer's disease increase with increase in age: 60s 15-20%, 70s 30-40%, and 80s 60%. That is, the situation becomes serious in 80s that one in every couple is to have Alzheimer's disease. There is no accurate statistical data in Korea yet; however knowing more than 12 million people suffer from the disease in Japan, the United States, and Europe, we can predict the numbers to grow fast in close future.

There are several reasons in the causes of Alzheimer's disease. First, the Alzheimer's disease is caused by the lowering concentration of neurotransmitter, acetylcholine. Acetylcholine having a quaternary amine structure is a neurotransmitter that, with acetylcholinesterase, is hydrolyzed to choline. According to the prior researches, the patients with Alzheimer's disease have low concentration of acetylcholine, and when acetylcholinesterase is inhibited, its concentration increases to improve the symptoms of Alzheimer's disease. Current medicinal substances used for treating Alzheimer's disease are synthetic acetylcholinesterase inhibitors such as Tarcrine (1) and Donepezil (2), illustrated in Formula 1. Another substance currently on clinical examination is Huperzine A, which is also an acetylcholinesterase inhibitor obtained from Hupersia Serrata.

(1)

<Formula 1>

(2)

<Formula 2>

Second, the Alzheimer's disease can be delayed in its progression by studying genetic factors of Alzheimer's disease that relate to β-amyloid synthesis, progression, accumulation of neuron, and β-amyloid settlement in the cortex. Likewise, by finding control actors for lowering β-amyloid concentration outside the cell and selectively removing β-amyloid settlement inside the brain, the Alzheimer's disease can be treated. β-amyloid aggregation is a substantial cause of Alzheimer's disease, thus active researches are done on the matter to suppress its forming.

Third, the Alzheimer's disease can be treated by using estrogen, an antioxidants, a free radical scavengers or anti-inflammatory agents. As a result, the disease progress can be prevented indirectly.

Fourth, the Alzheimer's disease can be treated by preventing gradual and irreversible degeneration of the synapse and neurons.

Currently, the therapeutics for Alzheimer's disease that have been approved by Food and Drug Administration (FDA) in the U.S. are all acetylcholinesterase inhibitors.

Among the therapeutics mentioned above, Tarcrine has side effects such as hepatotoxicity, abdominal spasm, vomiting, and diarrhea; moreover, it is efficacious to only about 25% of the patients with Alzheimer's disease. Meanwhile, Donepezil is more selective to acetylcholine, and has fewer side effects compared to Tarcrine; however, it is much less effective in treating the disease.

DETAILED DESCRIPTION OF THE INVENTION

The present invention relates to novel compounds having high selectivity to acetylcholinesterase, and having effective inhibition for aggregation of β-amyloid, and to provide the process for preparing them.

The present invention also relates to produce therapeutic substances for Alzheimer's disease comprising the above compounds.

In order to accomplish the objectives above, the present invention is provided with novel piperidine derivatives of Formula 3.

<Formula 3> wherein R' is benzyl or benzhydryl

R is (i) linear or branched $C_1$-$C_6$ alkyl, (ii)

or (iii) —$NHR_2$;

$R_1$ is —H, —OH, halogen, —$NO_2$, —$NH_2$, linear or branched $C_1$-$C_6$ alkyl;

$X_1$ is C;

$X_2$, $X_3$, $X_4$, $X_5$, and $X_6$ individually are CH or N; and $R_2$ is H or

In Formula 3, it is preferable that (i) when R is linear or branched $C_1$-$C_6$ alkyl, the R is —$CH_3$, or —$(CH_2)_nCH_3$ (wherein n is an integer raging from 2 to 5);

(ii) when R is the R is and (iii) when R is —$NHR_2$, the R is

The present inventor discovered through numerous researches and experiments that the novel piperidine derivative illustrated as Formula 3 has characteristics to treat Alzheimer's disease. Formula 3 above has basic structure of piperidine that comprises carboxyl group, wherein R and R' is substituted with various functional groups to strengthen the efficacy in treating Alzheimer's disease.

Reaction Scheme 1 represents the mechanism of inhibiting the function of acetylcholinesterase by binding enzyme acetylcholinesterase and ligand neostigmine. As shown in the Reaction Scheme 1, acetylcholinesterase that decomposes acetylcholine has functional anionic site and esteratic site, which is 6 Å apart from each other. The distance and interaction between the reaction sites are important factors for this enzyme to react with the ligand, thus the piperidine structure was planned so that a nitrogen atom on a piperidine ring would interact with an anionic site and an oxygen atom on an esteric group would interact with an esteratic site. Furthermore, by substituting the piperidine with various functional groups, the present invention validates structure-activity relations between a piperidine derivative and an acetylcholinesterase:

<Reaction Scheme 1>

Anionic site     Esteratic site

|← 6Å →|

Although the present invention can be synthesized by various synthetic processes, one example is described below comprising the steps of:

(a) reacting a compound of Formula 4 and a compound of Formula 5 to obtain a compound of Formula 6;
(b) reducing the compound of Formula 6 to obtain a compound of Formula 7;
(c) reacting the compound of Formula 7 with RCOOH or R—N=C=O to obtain a compound of Formula 3:

<Formula 4>

<Formula 5>

<Formula 6>

<Formula 7> wherein, the substitutions of R, R', R", $R_1$, $R_2$, $X_1$, $X_2$, $X_3$, $X_4$, $X_5$, $X_6$, and X are the same as stated above for Formula 3.

More particularly, the process can be illustrated as Reaction Scheme 2 below:

<Reaction Scheme 2>

R' = Benzyl, Benzhydryl           R' = Benzyl, Benzhydryl (Step 2) | LiAlH₄, Ether R' = Benzyl, Benzhydryl           R' = Benzyl, Benzhydryl The starting material represented by Formula 4 can be synthesized by various synthetic processes, or be purchased. One of conventional process for obtaining Formula 4 is shown in the Reaction Scheme 3 below:

The present invention also provides pharmaceutical composition comprising an effective amount of the piperidine derivative of Formula 3 or its pharmaceutically acceptable salts. The compound of Formula 3 can be comprised in the pharmaceutical composition as a pharmaceutically acceptable salt form, and acid-salt formed by pharmaceutically acceptable free acid is useful as its salt. That is, the compound of Formula 3 can be formed easily into pharmaceutically acceptable acid-salt by conventional method. An organic acid and inorganic acid can be used for free acid, wherein the inorganic acid is hydrochloric acid, bromic acid, sulfuric acid, or phosphoric acid, and the organic acid is substituted with citric acid, acetic acid, lactic acid, tartaric acid, maleic acid, fumaric acid, formic acid, propionic acid, oxalic acid, trifluoroacetic acid, benzoic acid, gluconic acid, methane sulfonic acid, glycolic acid, succinic acid, 4-toluene sulfonic acid, glutamic acid, aspartic acid, etc.

The pharmaceutical composition has inhibition effect of acetylcholinesterase and β-amyloid aggregation. The present invention of piperidine derivative can be both orally administrated in combination with a pharmaceutically acceptable carrier and injected with suitable solvent and diluent.

(1) Oral Administration

The present invention of piperidine derivative can be orally administrated as a form of a capsule or a tablet. Here, general excipients such as starch, lactose, talc, stearic acid magnesium, etc., are used for a capsule excipient. Any conventional excipient is also acceptable for tablets, because tablets are manufactured from granules. Moreover, other conventional carriers are all suitable.

In addition, additives such as starch, crystallized cellulose, hydroxypropylmethylcellulose, polyethylene glycol, lactose, polyvinyl pyrrolidone, glyceryl behanate, etc. and diluent such as glucose, spray-dried lactose, fast-flolactose, anhydrous lactose, sucrose, starch, starch 1500, calcium monohydrogen phosphate, emcompress, avicel, etc. can be added in the pharmaceutical composition for oral administration.

Wet binder and granule solutions such as water, ethanol, gelatin solution, starch paste solution, sucrose syrup, povidone, cellulose derivatives, etc. and lubricants such as polyethylene glycol 4000, 6000, 8000, sodium lauryl sulfate, magnesium lauryl sulfate, sodium benzoate, polyethylene monostearate, glyceryl triacetate, magnesium stearate, zinc stearate, calcium, stearic acid, talc, hardened vegitable oil, fluid paraffin, paraffin, etc. can be added in the composition for oral administration.

Fluidizing agents such as starch, talc, silicon dioxide, magnesium carbonate, magnesium oxide, etc. and adhesion inhibitors such as starch, talc, etc. and other additives such as hydroxypropylmethylcellulose, hydroxypropylcellulose, hydroxyethylcellulose, ethyl cellulose, methyl cellulose, carboxymethyl cellulose, polyacrylic acid, acrylic acid, acrylic acid derivative, polyvinyl pyrrolidone, polyethylene glycol, etc. can be added in the composition for oral administration.

(2) Injection

Meanwhile, in case of injection, the solvents such as alcohol derivatives, higher fatty acid ester, etc. and diluents comprising phosphate buffer saline and physiological saline and antiseptics such as sodium benzoate, methylparaben, or propylparaben can be added in the pharmaceutical composition for injection.

For example, the pharmaceutical composition for injection can be manufactured by dissolving the piperidine derivative in an alcohol, and diluting it with either phosphate buffer saline or physiological saline.

Dosage

An effective amount of the compound of Formula 3 according to the present invention is generally 0.01~500 mg/kg for adult. Furthermore, with doctors prescription, this dosage can be divided into 1~6 edible amount per day.

For the reference, various literatures, which are related to the present invention, are cited as follows. These references compose the present invention in combination with the invention, and some of the background and detailed descriptions are quoted from these references.

[1] Wurtman, R. J. *Sci. Am.* 1985, 252, 48.

[2] Davies, P.; Maloney, A. J. F. *Lancet* 1796, 2, 1404

[3] Bowen, D. M.; Smith, C. B.; White, P.; Dawson, A. N. *Brain* 1976, 99, 459

[4] Albert, A.; Gledhill, W. J. *J. soc. Chem. Ind.* 1945, 64, 169

[5] Sugimoto, H.; Iimura, Y.; Yamanishi, Y.; Yamatsu, K. *J. Med. Chem.* 1995, 38, 4821

[6] Murphy, M. F.; Hardiman, S. T.; Nash, R. J.; Huff, F. J.; Demkovich, J. J.; Dobson, C.; Knappe, U. E. *Ann. N. Y. Acadd. Sci.* 1991, 640, 253

[7] Huff, F. J.; Antuno, P.; Murphy, M.; Beyer, J.; Dobson, C. *Ann. N. Y. Acad. Sci.* 1991, 640, 263

[8] Volger, B. W. *Clin. Pharm.* 1991, 10, 447

[9] Rupniak, N. M.; Tye, S. J.; Brazeil, C.; Heald, A.; Iverson, S. D.; Pagella, P. G.; *J. Neurol. Sci.* 1992, 107, 246

[10] Chen, Y. L.; Nielsen, J.; Hedberg, K.; Dunaiskis, A.; Jones, S.; Russo, L.; Johnson, J.; Ives, J.; Liston, D. *J. Med. Chem.* 1992, 35, 1429

[11] Thomsen, T.; Bickel, U.; Fischer, J. P.; Kewitz, H. *Dementia,* 1990, 1, 46

[12] Dal-Bianco, P.; Maly, J.; Wobwer, C.; Lind, C.; Koch, G.; Hufgard, J.; Marschall, I.; Mraz, M.; Deecke, L. *J. Neural. Trasm. Suppl.(Austria),* 1991, 33, 59

[13] Giacobini, E.; Becker, R. *Clin. Neuropharmacol.* 1990, 13 (suppl2), 577

[14] Kozikowski, A. P.; Theils, E.; Tang, X. C.; Hanin, I. *Adv. med. Chem.* 1992, 1, 175

[15] Hulme, E. C.; Birdsall. N. J. M.; Buckley, N. J. *Ann. Rev. Pharmacol. Toxicol.* 1990, 30, 633
[16] Mei, L.; Roeske, W. R.; Yamamura, H. I. *Life Sci.* 1989, 45, 1831
[17] Raffaele, K. C.; Berardi, A.; Asthana, S.; Morris, P.; Haxby, J. V.; soncart, T. T. *Psychopharmacol. Bull.* 1991, 27, 315
[18] Kumar. v.; Calache, M. Int. *J. Clin. Pharmacol. Ther. Toxicol.* 1991, 29, 23
[19] Gray, J. A.; Enz, A.; Spiegel, R. *Trends Pharmacol. Sci.* 1989, 85
[20] Traub, M.; Freedman, S. B. *Dementia,* 1992, 3, 189
[21] Rupniak, N. M. J.; Iverson, S. J.; Iverson S. D. *J. Neurol. Sci.* 1992, 110, 222
[22] Sauerberg, P.; Olsen, P. H.; Nielsen, S.; Treppendahl, s.; sheardown, M. J.; Honore, T.; Mitch, C. H.; Ward, J. S.; Pike, A. J.; Bymaster, F. P.; Sawyer, B. D.; Shanon, H. E. *J. Med. Chem.* 1992, 35, 2274
[23] Sapiro, G.; Floersheim, P.; Boelsterli, j.; Amstutz, R; Bolliger, G.; Gammenthaler, H.; Gmelin, G.; Supavilai, P.; Walkinshaw, M. *J. Med. Chem.* 1992, 35, 15
[24] Nilsson, B. M.; Vargas, H. M.; Hacksell, U. *J. Med Chem.* 1992, 35, 3270
[25] Pang, Y. P.; Quiram, P.; Jelacic, T.; hong, F.; Brimijoin, S. *J. Biol. Chem.* 1996, 271, 23646
[26] Mckenna, M. T.; proctoer, G. R.; Young, l. C.; Harvey, A. L. *J. Med. Chem.* 1997, 40, 3516
[27] Rampa, A.; bisi, A.; Valenti, P.; Recanatini, M.; Cavalli, a.; andrisano, V.; Cavrini, V.; Fin, L.; Buriani, A.; Giusti, P. *J. Med. Chem.* 1998, 41, 3976
[28] Badia, A.; Banos, J. E.; Camps, P.; Contreas, J.; Gorbig, d. M.; Munoz-Torrero, D.; Simon, M.; Vivas, N. M. *Bioorg. Med. Chem.* 1998, 6, 427
[29] Suzuki, T.; Usui, T.; Oka, M.; suzuki, ts.; Kataoka, T. *Chem. Pharm. Bull.* 1998, 46(8), 1265
[30] Suzuki, T.; Uesaka H.; Hamajima, H.; Ikami, T.; *Chem Pharm Bull* 1999, 47(6), 87
[31] Messer, Jr. W. S.; Abuh, Y. F.; Liu, Y.; Periyasamy, S.; Ngur, D. O.; Edgar, M. A. N.; El-Assadi S. S., A. A.; Dunbar, P. G.; Roknich, S.; Rho, T.; Fang, Z.; Ojo, B.; Zhang, H.; Huzl, III, J. J.; Nagy, p. I. *J. Med. Chem.* 1997, 40, 1230
[32] Yu, Q.-S.; holloway, H. W.; utsuki, T.; Brossi, a.; Greig. N. H. *J. Med. Chem.* 1999, 42, 1855
[33] Al-Jafari, A.; Kamal, M.; Grieg, N.; Alhomida, A.; Perry, E. *Biochem. Biophy. Res. Comm.* 1998, 248, 180
[34] Ellman, G.; Courtney, D.; Andres, V.; Featherstone, R. *Biochem. Pharm.* 1961, 7, 88
[35] Jeyarasasingam, G.; Yeluashvili, M.; Quik, M. *Neuropharm.* 2000, 11, 1173
[36] Kuno, F.; Otoguro, K.; Shiomi, K.; Iwai, Y.; Omura, S. *J. Antibiotics* 1996, 49, 742
[37] Ehrenstein, G; Galdzicki, Z.; Lange, G. D. *Biophys. J.* 1997, 73, 1276
[38] Kiely, J.; Moos, W.; Pavia, M.; Schwarz, R.; Woodard, G. *Anal. Biochem.* 1991, 196, 439
[39] Kamal, M.; Greig, N.; Alhomida, A.; Al-Jafari, A. *Biochem. Pharm.* 2000, 60, 561

PREPERATION OF PIPERIDINE DERIVATIVES

EXAMPLE 1

Step 1

The Synthesis of Ethyl-4-[4-(benzhydryloxy)piperidino]butanoate

Figure 1:
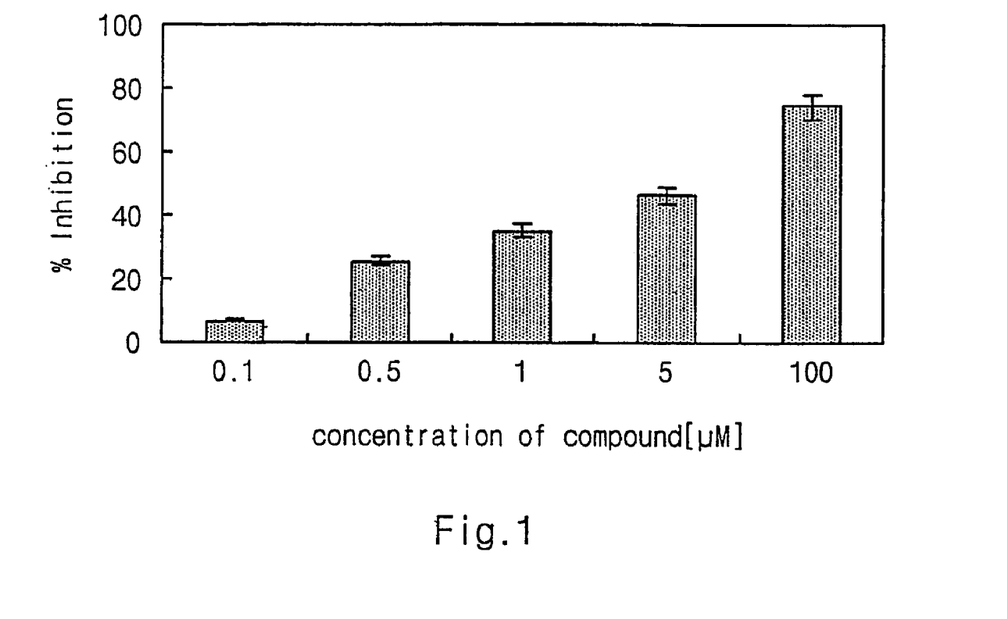
FIG. 1 is a graph illustrating inhibition of acetylcholinesterase activation of piperidine derivatives obtained from Example 1 according to the present invention.
Figure 2:
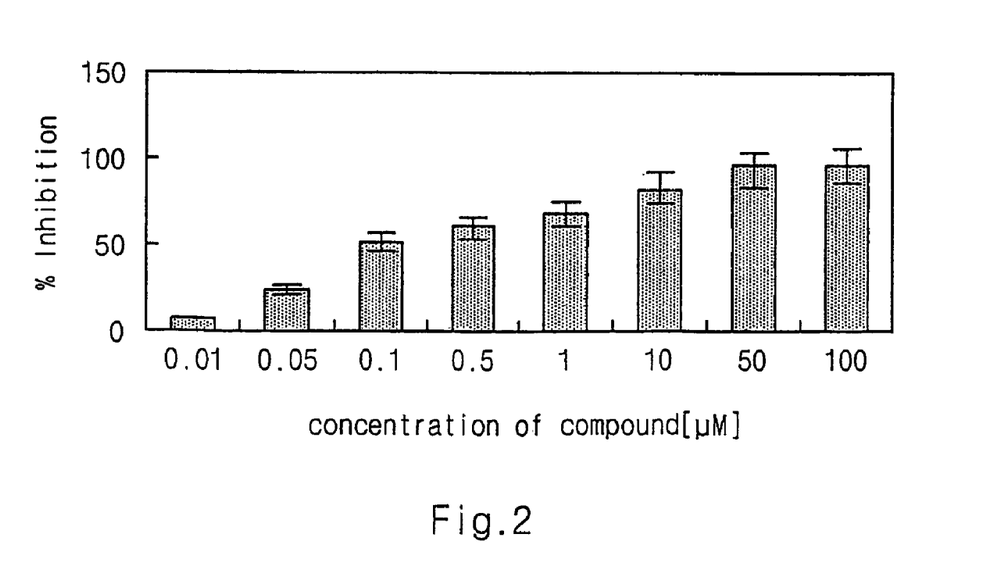
FIG. 2 is a graph illustrating inhibition of acetylcholinesterase activation of piperidine derivatives obtained from Example 2 according to the present invention.
Figure 3:
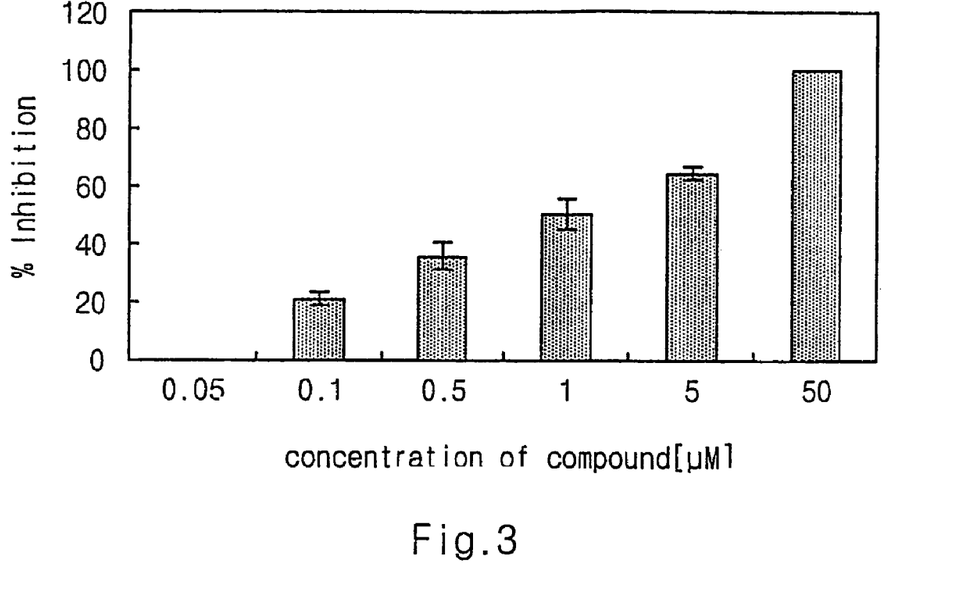
FIG. 3 is a graph illustrating inhibition of acetylcholinesterase activation of piperidine derivatives obtained from Example 3 according to the present invention.
Figure 4:
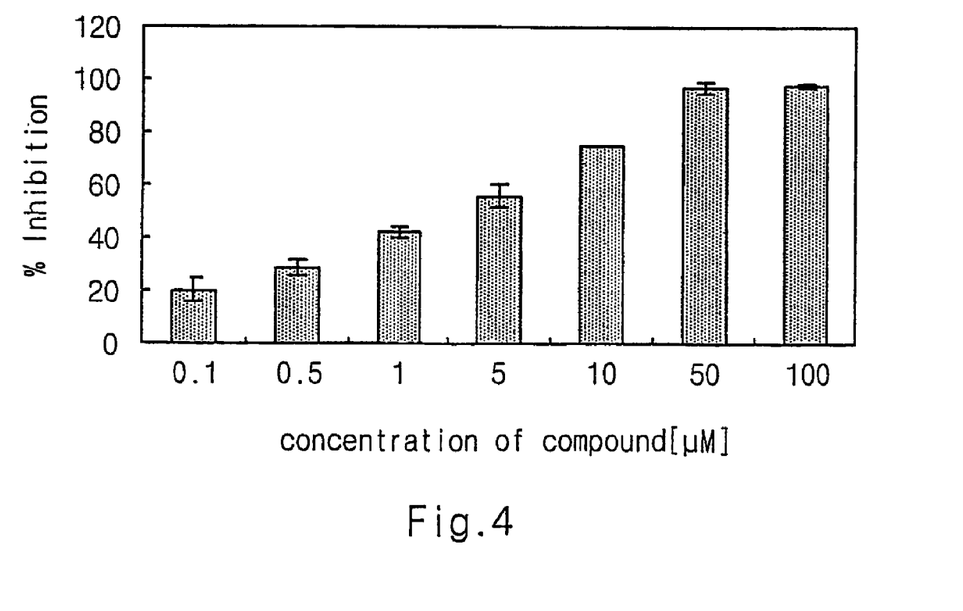
FIG. 4 is a graph illustrating inhibition of acetylcholinesterase activation of piperidine derivatives obtained from Example 4 according to the present invention.
Figure 5:
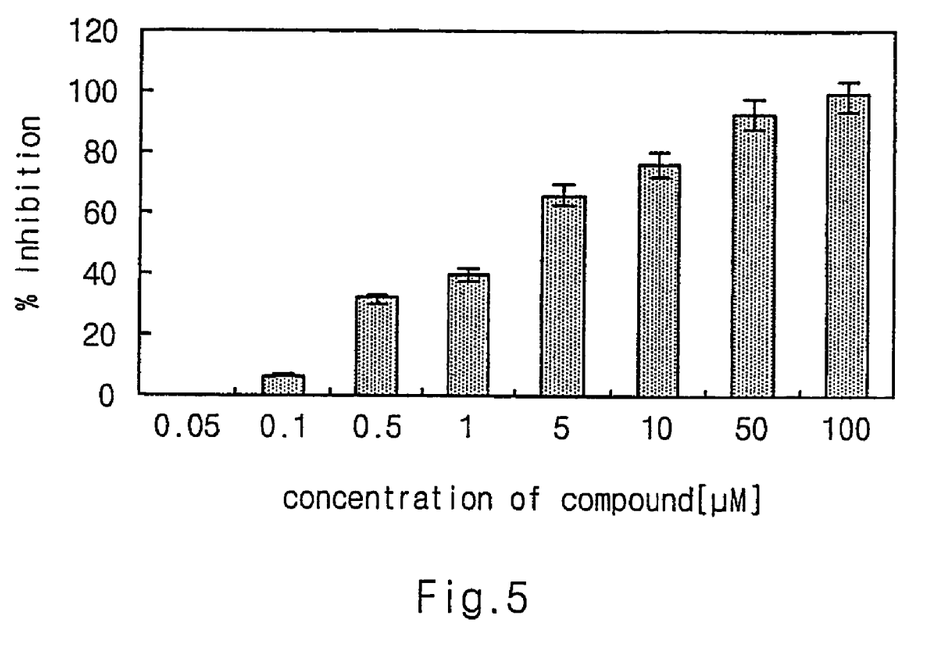
FIG. 5 is a graph illustrating inhibition of acetylcholinesterase activation of piperidine derivatives obtained from Example 5 according to the present invention.

To 28 mL of methyl isobutyl keton (MIBK) was added 4-(benzhydryloxy)piperidine (1.5 g), $NaHCO_3$ (1.42 g), potassium iodide (catalyst), and ethyl-4-chlorobutyrate (1.2 mL). The resulting mixture was refluxed for 4 hrs. The resulting mixture was cooled, and concentrated under reduced pressure. The resultant solution was then extracted by using water and chloroform. An organic solution layer was dehydrated over magnesium sulfate, filtered, and concentrated under reduced pressure. The column chromatography was performed thereon, thereby obtaining crude yellowish liquid product (1.41 g, 66% yield) of the title.

$^1$H-NMR($CDCl_3$): δ1.26 (t, J=15.2 Hz, 3H) 1.77-1.93 (m, 6H) 2.21-2.30 (m, 2H) 2.32-2.42 (m, 4H) 2.77-2.79 (m, 2H) 3.41-3.44 (m, 1H) 4.14 (q, J=15.2 Hz, 2H) 5.53 (s, 1H) 7.23-7.37 (m, 10H)

Step 2

Synthesis of 4-[4-(benzhydryloxy)piperidino]-1-butanol

The compound obtained from step 1 (0.4 g) was dissolved in ether, and cooled in an ice bath. $LiAlH_4$ (0.1 g) was added slowly to the solution. The resulting mixture was reacted at room temperature for 1 hr. before adding water to end the reaction. The resulting solution was then extracted by using water and ester. An organic solution layer was dehydrated over magnesium sulfate, filtered, and concentrated under reduced pressure. The column chromatography was performed thereon, thereby obtaining crude yellowish liquid product (0.15, 43% yield) of the title.

$^1$H-NMR($CDCl_3$): δ1.68-1.77 (m, 4H) 1.78-1.94 (m, 4H) 2.27-2.38 (m, 4H) 2.76-2.79 (m, 2H) 3.45-3.58 (m, 3H) 5.51 (s, 1H) 7.23-7.36 (m, 10H)

Step 3

Synthesis of 4-[4-(benzhydryloxy)piperidino]butyl-4-nitrobenzoate

To 4 mL of chloroform was added 4-[4-benzhydryloxy] piperidino]-1-butanol obtained from step 2 (0.11 g), 4-nitrobenzoic acid (0.1 g), 4-dimethylaminopyridine (DMAP, 0.12 g), and 1-[3-(dimethylamino)propyl]-3-ethylcarbodimide hydrochloride (0.1 g). The resulting mixture was allowed to react at room temperature for 3 hrs. before adding water to end the reaction. The resulting solution was acidified with 1N hydrochloric acid, and extracted by using chloroform.

An organic solution layer was washed with 1N sodium hydroxide, dehydrated over magnesium sulfate, filtered, and concentrated under reduced pressure. The column chromatography was performed thereon, thereby obtaining crude yellowish liquid product (0. 12 g, 76% yield) of the title.

$^1$H-NMR(CDCl$_3$): δ1.65-1.89 (m, 8H) 2.06-2.16 (m, 2H) 2.39 (t, J=14.8 Hz, 2H) 2.74-2.77 (m, 2H) 3.45-3.48 (m, 1H) 4.40 (t, J=12.9 Hz, 2H) 5.53 (s, 1H) 7.23-7.37 (m, 2H) 8.21 (d, J=8.8 Hz, 2H) 8.29 (d, J=8.7 Hz, 2H)

EXAMPLE 2

The Synthesis of 4-[4-(benzhydryloxy)piperidino] butyl-4-chlorobenzoate

To 5 mL of chloroform was added 4-[4-benzhydryloxy] piperidino]-1-butanol, which was obtained from step 2 of example 1 (0.15 g), 4-chlorobenzoic acid (0.11 g), 4-dimethylaminopyridine (0.16 g), 1-[3-(dimethylamino)propyl]-3-ethylcarboimide hydrochloric acid (0.1 g),. The resulting mixture was allowed to react at room temperature for 2 hrs. before adding water to end the reaction. The resulting solution was acidified with 1N hydrochloric acid, and extracted by using chloroform. An organic solution layer was washed with 4N sodium hydroxide, dehydrated over magnesium sulfate, filtered, and concentrated under reduced pressure. The column chromatography was performed thereon, thereby obtaining crude yellowish liquid product (0.15 g, 71% yield) of the title.

$^1$H-NMR(CDCl$_3$): 1.62-1.90 (m, 8H) 2.14-2.22 (m, 2H) 2.39 (t, J=14.9 Hz, 2H) 3.45-3.51 (m, 1H) 4.3 (t, J=12.7 Hz, 2H) 5.53 (s, 1H) 7.27-7.37 (m, 10H) 7.41 (d, J=8.5 Hz, 2H) 7.97 (d, J=8.5 Hz, 2H)

EXAMPLE 3

The Synthesis of 4-[4-(benzhydryloxy)piperidino]butyl 4-fluorobenzoate

To 5 mL of chloroform was added 4-[4-benzhydryloxy] piperidino]-1-butanol, which was obtained from step 2 of example 1 (0.16 g), 4-fluorobenzoic acid (0.1 g), 4-dimethylaminopyridine (0.17 g), 1-[3-(dimethylamino)propyl]-3-ethylcarboimide hydrochloric acid (0.1 g). The resulting mixture was allowed to react at room temperature for 2 hrs. before adding water to end the reaction. The resulting solution was acidified with 1N hydrochloric acid, and extracted by using chloroform. An organic solution layer was washed with 4N sodium hydroxide, dehydrated over magnesium sulfate, filtered, and concentrated under reduced pressure. The column chromatography was performed thereon, thereby obtaining yellowish liquid product (0.16 g, 74% yield) of the title.

$^1$H-NMR(CDCl$_3$): 1.61-1.89 (m, 8H) 2.11-2.14 (m, 2H) 2.34 (t, J=15.2 Hz, 2H) 2.69-2.77 (m, 2H) 3.38-3.45 (m, 1H) 4.29 (t, J=13.2 Hz, 2H) 5.50 (s, 1H) 7.07 (t, J=22.8 Hz, 2H) 7.21-7.39 (m, 10H) 8.02 (d,d J=19.6 Hz, 2H)

EXAMPLE 4

The Synthesis of 4-[4-(benzhydryloxy)piperidino]butyl benzoate

To 6 mL of chloroform was added 4-[4-benzhydryloxy] piperidino]-1-butanol, which was obtained from step 2 of example 1 (0.21 g), benzoic acid (0.11 g), 4-dimethylaminopyridine (0.23 g), 1-[3-(dimethylamino)propyl]-3-ethylcarboimide hydrochloric acid (0.13 g). The resulting mixture was allowed to react at room temperature for 2 hrs. before adding water to end the reaction. The resulting solution was acidified with 1N hydrochloric acid, and extracted using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.17 g, 63% yield) of the title.

$^1$H-NMR(CDCl$_3$): 1.67-1.91 (m, 8H) 2.12-2.20 (m, 2H) 2.40 (t, J=15.0 Hz, 2H) 2.77-2.80 (m, 2H) 3.44-3.50 (m, 1H) 4.35 (t, J=12.7 Hz, 2H) 5.54 (s, 1H) 7.25-7.37 (m, 10H) 7.42-7.47 (m, 2H) 7.54-7.57 (m, 1H) 8.05 (d, J=8.5 Hz, 2H)

EXAMPLE 5

The Synthesis of 4-[4-(benzhydryloxy)piperidino]butyl 4-isopropylbenzoate

To 12 mL of chloroform was added 4-[4-benzhydryloxy] piperidino]-1-butanol, which was obtained from step 2 of example 1 (0.3 g), 4-isopropylbenzoic acid (0.22 g), 4-dimethylaminopyridine (0.32 g), 1-[3-(dimethylamino)propyl]-3-ethylcarboimide hydrochloric acid (0.19 g). The resulting mixture was allowed to react at room temperature for 3 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.28 g, 66% yield) of the title.

$^1$H-NMR(CDCl$_3$): 1.24 (d, J=14.4 Hz, 6H) 1.58-1.86 (m, 8H) 2.04-2.18 (m, 2H) 2.34 (t, J=15.2 Hz, 2H) 2.72-2.78 (m, 2H) 2.97-2.90 (m, 1H) 3.46-3.40 (m, 1H) 4.28 (t, J=19.6 Hz, 2H) 5.50 (s, 1H) 7.34-7.19 (m, 12H) 7.93 (d, J=16.0 Hz, 2H)

EXAMPLE 6

The Synthesis of 4-[4-(benzhydryloxy)piperidino]butyl 4-(tert-butyl)benzoate

To 5 mL of chloroform was added 4-[4-benzhydryloxy] piperidino]-1-butanol, which was obtained from step 2 of example 1 (0.15 g), 4-tert-butylbenzoic acid (0.12 g), 4-dimethylaminopyridine (0.16 g), 1-[3-(dimethylamino)propyl]-3-ethylcarboimide hydrochloric acid (0.1 g). The resulting mixture was allowed to react at room temperature for 3 hrs. before adding water to end the reaction. The reaction mixture was acidified with 1N hydrochloric acid, and extracted by using methylene chloride. An organic solution layer was washed with 1N sodium hydroxide, dehydrated over sodium sulfate anhydrous, filtered, and concentrated under reduced pressure. The column chromatography was performed thereon, thereby obtaining crude yellowish liquid product (0.19 g, 96% yield) of the title.

$^1$H-NMR(CDCl$_3$): 1.41 (s, 9H) 1.72-1.86 (m, 8H) 2.05-2.15 (m, 2H) 2.34 (t, J=14.6 Hz, 2H) 2.71-2.77 (m, 2H) 3.39-3.47 (m, 1H) 4.3 (t, J=12.5 Hz, 2H) 5.51 (s, 1H) 7.21-7.37 (m, 10H) 7.42 (d, J=8.74 Hz, 2H) 7.96 (d, J=10.56 Hz, 2H)

EXAMPLE 7

The Synthesis of 4-[4-(benzhydryloxy)piperidino]butyl 3-chlorobenzoate

To 6 mL of chloroform was added 4-[4-benzhydryloxy] piperidino]-1-butanol, which was obtained from step 2 of example 1 (0.2 g), 3-chlorobenzoic acid (0.14 g), 4-dimethylaminopyridine (0.22 g), 1-[3-(dimethylamino)propyl]-3-ethylcarboimide hydrochloric acid (0.13 g). The resulting mixture was allowed to react in room temperature for 4 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.092 g, 33% yield) of the title.

$^1$H-NMR(CDCl$_3$): 1.57-1.92 (m, 8H) 2.10-2.18 (m, 2H) 2.34 (t, J=14.8 Hz, 2H) 2.73-2.79 (m, 2H) 3.41-3.48(m, 1H) 4.31 (t, J=12.8 Hz, 2H) 5.50 (s, 1H) 7.20-7.39 (m, 11H) 7.50 (d, J=8 Hz, 1H) 7.89 (d, J=7.6 Hz, 1H) 7.98 (s, 1H)

EXAMPLE 8

The Synthesis of 4-[4-(benzhydryloxy)piperidino]butyl 3-fluorobenzoate

To 6 mL of chloroform was added 4-[4-benzhydryloxy] piperidino]-1-butanol, which was obtained from step 2 of example 1 (0.21 g), 3-fluorobenzoic acid (0.13 g), 4-dimethylaminopyridine (0.23 g), 1-[3-(dimethylamino)propyl]-3-ethylcarboimide hydrochloric acid (0.13 g). The resulting mixture was allowed to react at room temperature for 3 hrs. before adding water to end the reaction. The resulting solution was acidified with 1N hydrochloric acid, and extracted by using chloroform. The organic layer was washed with 1N sodium hydroxide, dehydrated over magnesium sulfate, filtered, and concentrated under reduced pressure. The column chromatography was performed thereon, thereby obtaining crude yellowish liquid product (0.0388 g, 14% yield) of the title.

$^1$H-NMR(CDCl$_3$): 1.66-1.92 (m, 8H) 2.17-2.24 (m, 2H) 2.40 (t, J=14.4 Hz, 2H) 2.76-2.82 (m, 2H) 3.44-3.49 (m, 1H) 4.35 (t, J=12.8 Hz, 2H) 5.53 (s, 1H) 7.23-7.43 (m, 12H) 7.72(d, J=7.7 Hz, 1H) 7.84 (d, J=7.7 Hz, 1H)

EXAMPLE 9

The Synthesis of 4-[4-(benzhydryloxy)piperidino]butyl N-(4-chlorophenyl)carbamate To 19 mL of acetonitrile was added 4-[4-benzhydryloxy] piperidino]-1-butanol, which was obtained from step 2 of example 1 (0.66 g), 4-chlorophenyl isocyanate (0.3 g). The resulting mixture was refluxed for 4 hrs. The reaction mixture was cooled, and concentrated under reduced pressure. The resultant mixture was then extracted by using water and chloroform. An organic solution layer was dehydrated over magnesium sulfate, filtered, and concentrated under reduced pressure. The column chromatography was performed thereon, thereby obtaining crude yellowish liquid product (0.23 g, 24% yield) of the title.

$^1$H-NMR(CDCl$_3$): 1.68-1.94 (m, 6H) 2.04-2.12 (m, 2H) 2.22-2.28 (m, 2H) 2.43 (t, J=13.4 Hz, 2H) 2.76-2.82 (m, 2H) 3.47-3.51 (m, 1H) 4.18 (t, J=10.8 Hz, 2H) 5.52 (s, 1H) 6.85 (s, 1H) 7.24-7.43 (m, 14H)

EXAMPLE 10

The Synthesis of 4-[4-(benzhydryloxy)piperidino]butyl N-(4-fluorophenyl)carbamate To 14 mL of acetonitrile was added 4-[4-benzhydryloxy] piperidino]-1-butanol, which was obtained from step 2 of example 1 (0.48 g), 4-fluorophenyl isocyanate (0.23 g). The mixture was refluxed for 4 hrs. The reaction mixture was cooled, and concentrated under reduced pressure. The resultant mixture was then extracted by using water and chloroform. An organic solution layer was dehydrated over magnesium sulfate, filtered, and concentrated under reduced pressure. The column chromatography was performed thereon, thereby obtaining crude yellowish liquid product (0.18 g, 24% yield) of the title.

$^1$H-NMR(CDCl$_3$): 1.66-1.92 (m, 6H) 1.81-1.97 (m, 2H) 2.09-2.16 (m, 2H) 2.31 (t, J=12.2 Hz, 2H) 2.74-2.82 (m, 2H) 3.39-3.42 (m, 1H) 4.12 (t, J=11.2 Hz, 2H) 5.49 (s, 1H) 6.67 (s, 1H) 6.98 (t, J=10.6 Hz, 2H) 7.14-7.25 (m, 12H)

EXAMPLE 11

The Synthesis of 4-[4-(benzhydryloxy)piperidino]butyl nitcotinate

To 8 mL of chloroform was added 4-[4-benzhydryloxy] piperidino]-1-butanol, which was obtained from step 2 of example 1 (0.14 g), nicotinic acid (0.1 g), 4-dimethylaminopyridine (0.12 g), 1-[3-(dimethylamino)propyl]-3-ethylcarboimide hydrochloric acid (0.1 g). The mixture was allowed to react at room temperature for 3 hrs. before adding water to end the reaction. The reaction mixture was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.12 g, 66% yield) of the title.

$^1$H-NMR(CDCl$_3$): 1.64-1.89 (m, 8H) 2.14-2.17 (m, 2H) 2.38 (t, J=14.9 Hz, 2H) 2.75-2.78 (m, 2H) 3.46-3.51 (m, 1H) 4.38 (t, J=12.9 Hz, 2H) 5.53 (s, 1H) 7.24-7.39 (m, 11H) 8.35 (d, J=4.9 Hz, 1H) 8.78 (d, J=4.8 Hz, 1H) 9.23 (s, 1H)

EXAMPLE 12

Step 1

The Synthesis of ethyl 4-[4-(benzyloxy)piperidino]butanoate

To 12 mL of N,N-dimethylformamide was added 4-(benzyloxy)piperidine (0.8 g), sodium bicarbonate (1.05 g), potassium iodide (used as a catalyst), ethyl-4-chlorobutyrate (0.88 mL). The resulting mixture was refluxed for 4 hrs. The resulting mixture was cooled, and concentrated under reduced pressure. The resultant mixture was then extracted by using water and chloroform. An organic solution layer was dehydrated over magnesium sulfate, filtered, and concentrated under reduced pressure. The column chromatography was performed thereon, thereby obtaining crude yellowish liquid product (1.05 g, 82% yield) of the title.

$^1$H-NMR(CDCl$_3$): 1.22 (t, J=16.8 Hz, 3H) 1.67-1.91 (m, 6H) 2.09-2.19 (m, 2H) 2.27-2.36 (m, 4H) 2.78-2.81 (m, 2H) 3.38-3.42 (m, 1H) 4.10 (q, J=16.8 Hz, 2H) 4.51 (s, 2H) 7.23-7.34 (m, 5H)

Step 2

The Synthesis of
4-[4-(benzyloxy)piperidino]-1-butanol

The compound obtained from step 1 (4.8 g) was dissolved in ether, and cooled in an ice bath. LialH$_4$ (0.1 g) was added slowly to the solution. The resulting mixture was reacted at room temperature for 1 hr. before adding water to end the reaction. The resulting solution was then extracted by using water and ester. An organic solution layer was dehydrated over magnesium sulfate, filtered, and concentrated under reduced pressure. The column chromatography was performed thereon, thereby obtaining crude yellowish liquid product (3.44 g, 83% yield) of the title.

$^1$H-NMR(CDCl$_3$): 1.62-1.76 (m, 6H) 1.84-1.91 (m, 2H) 2.21-2.31 (m, 4H) 2.70-2.76 (m, 2H) 3.42-3.56 (m, 3H) 4.48 (s, 2H) 7.19-7.30 (m, 5 H)

Step 3

The Synthesis of 4-[4-(benzyloxy)piperidino]butyl
4-nitrobenzoate

To 14 mL of chloroform was added 4-[4-(benzyloxy)piperidino]-1-butanol, which was obtained from step 2 (0.37 g), 4-nitrobenzoic acid (0.35 g), 4-dimethylaminopyridine (0.51 g), 1-[3-(dimethylamino)propyl]-3-ethylcarboimide hydrochloric acid (0.3 g). The resulting mixture was allowed to react at room temperature for 2 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.58 g, 64% yield) of the title.

$^1$H-NMR(CDCl$_3$): 1.64-1.91 (m, 8H) 2.12-2.18 (m, 2H) 2.40 (t, J=14.9 Hz, 2H) 2.76-2.82 (m, 2H) 3.42-3.48 (m, 1H) 4.40 (t, J=12.9 Hz, 2H) 4.55 (s, 1H) 7.27-7.36 (m, 5H) 8.21 (d, J=10.7 Hz, 2H) 8.29 (d, J=10.6 Hz, 2H)

EXAMPLE 13

The Synthesis of 4-[4-(benzyloxy)piperidino]butyl
4-chlorobenzoate

To 30 mL of chloroform was added 4-[4-(benzyloxy)piperidino]-1-butanol, which was obtained from step 2 of example 12 (0.8 g), 4-chlorobenzoic acid (0.71 g), 4-dimethylaminopyridine (0.64 g), 1-[3-(dimethylamino)propyl]-3-ethylcarboimide hydrochloric acid (1.11 g). The resulting mixture was allowed to react at room temperature for 4 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.74 g, 61% yield) of the title.

$^1$H-NMR(CDCl$_3$): 1.68-1.94 (m, 8H) 2.15-2.22 (m, 2H) 2.40 (t, J=14.7 Hz, 2H) 2.78-2.84 (m, 2H) 3.42-3.46 (m, 1H) 4.34 (t, J=12.6 Hz, 2H) 4.56 (s, 2H) 7.28-7.37 (m, 5H) 7.42 (d, J=8.4 Hz, 2H) 7.98 (d, J=8.4 Hz, 2H)

EXAMPLE 14

The Synthesis of 4-[4-(benzyloxy)piperidino]butyl
4-fluorobenzoate

To 14 mL of chloroform was added 4-[4-(benzyloxy)piperidino]-1-butanol, which was obtained from step 2 of example 12 (0.37 g), 4-fluorobenzoic acid (0.3 g), 4-dimethylaminopyridine (0.51 g), 1-[3-(dimethylamino)propyl]-3-ethylcarboimide hydrochloric acid (0.3 g). The resulting mixture was allowed to react at room temperature for 2 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.34 g, 63% yield) of the title.

$^1$H-NMR(CDCl$_3$): 1.61-1.78 (m, 6H) 1.84-1.90 (m, 2H) 2.10-2.16 (m, 2H) 2.34 (t, J=15.2 Hz, 2H) 2.71-2.78 (m, 2H) 3.38-3.44 (m, 1H) 4.29 (t, J=13.2 Hz, 2H) 4.51 (s, 2H) 7.07 (t, J=23.2 Hz, 2H) 7.21-7.34 (m, 5H) 8.02 (d,d J=20.0 Hz, 2H)

EXAMPLE 15

The Synthesis of 4-[4-(benzyloxy)piperidino]butyl
benzoate

To 14 mL of chloroform was added 4-[4-(benzyloxy)piperidino]-1-butanol, which was obtained from step 2 of example 12 (0.3 g), benzoic acid (0.26 g), 4-dimethylaminopyridine (0.51 g), 1-[3-(dimethylamino)propyl]-3-ethylcarboimide hydrochloric acid (0.3 g). The resulting mixture was allowed to react at room temperature for 2 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.35 g, 69% yield) of the title.

$^1$H-NMR(CDCl$_3$): 1.58-1.79 (m, 6H) 1.88-1.96(m, 2H) 2.08-2.16 (m, 2H) 2.35 (t, J=15.2 Hz, 2H) 2.74-2.78 (m, 2H) 3.36-3.44 (m, 1H) 4.30 (t, J=13.2 Hz, 2H) 4.51 (s, 2H) 7.21-7.33 (m, 5H) 7.38-7.45 (m, 2H) 7.50-7.54 (m, 1H) 8.01 (d, J=9.6 Hz, 2H)

EXAMPLE 16

The Synthesis of 4-[4-(benzyloxy)piperidino]butyl
4-isopropylbenzoate

To 20 mL of chloroform was added 4-[4-(benzyloxy)piperidino]-1-butanol, which was obtained from step 2 of example 12 (0.63 g), 4-isopropylbenzoic acid (0.59 g), 4-dimethylaminopyridine (0.50 g), 1-[3-(dimethylamino)propyl]-3-ethylcarboimide hydrochloric acid (0.88 g). The resulting mixture was allowed to react at room temperature for 3 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.62 g, 64% yield) of the title.

$^1$H-NMR(CDCl$_3$): 1.24 (d, J=8.2 Hz, 6H) 1.63-1.77 (m, 6H) 1.80-1.94 (m, 2H) 2.10-2.14 (m, 2H) 2.39 (t, J=14.9 Hz, 2H) 2.76-2.81 (m, 2H) 2.90-2.97(m, 1H) 3.38-3.44 (m, 1H) 4.33 (t, J=12.7 Hz, 2H) 4.56 (s, 2H) 7.29-7.37 (m, 12H) 7.94 (d, J=8.2 Hz, 2H)

EXAMPLE 17

The Synthesis of 4-[4-(benzyloxy)piperidino]butyl 4-(tert-butyl)benzoate

To 30 mL of chloroform was added 4-[4-(benzyloxy)piperidino]-1-butanol, which was obtained from step 2 of example 12 (0.35 g), 4-tert-butylbenzoic acid (0.36 g), 4-dimethylaminopyridine (0.49 g), 1-[3-(dimethylamino)propyl]-3-ethylcarboimide hydrochloric acid (0.28 g). The resulting mixture was allowed to react at room temperature for 2 hrs. before adding water to end the reaction. The resulting solution was acidified with 1N hydrochloric acid, and extracted by using chloroform. An organic solution layer was washed with 1N sodium hydroxide, dehydrated over sodium sulfate anhydrous, filtered, and concentrated under reduced pressure. The column chromatography was performed thereon, thereby obtaining crude yellowish liquid product (0.42 g, 76% yield) of the title.

$^1$H-NMR(CDCl$_3$): 1.32 (s, 9H) 1.64-1.78 (m, 6H) 1.86-1.92 (m, 2H) 2.08-2.14 (m, 2H) 2.35 (t, J=15.2 Hz, 2H) 2.72-2.77 (m, 2H) 3.37-3.41 (m, 1H) 4.29 (t, J=12.8 Hz, 2H) 4.51 (s, 2H) 7.23-7.36 (m, 5H) 7.42 (d, J=8.0 Hz, 2H) 7.94 (d, J=8.0 Hz, 2H)

EXAMPLE 18

The Synthesis of 4-[4-(benzyloxy)piperidino]butyl 3-chlorobenzoate

To 12 mL of chloroform was added 4-[4-(benzyloxy)piperidino]-1-butanol, which was obtained from step 2 of example 12 (0.43 g), 3-chlorobenzoic acid (0.38 g), 4-dimethylaminopyridine (0.60 g), 1-[3-(dimethylamino)propyl]-3-ethylcarboimide hydrochloric acid (0.34 g). The resulting mixture was allowed to react at room temperature for 4 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.31 g, 47% yield) of the title.

$^1$H-NMR(CDCl$_3$): 1.57-1.77 (m, 6H) 1.89-1.96 (m, 2H) 2.08-2.14 (m, 2H) 2.31 (t, J=14.8 Hz, 2H) 2.71-2.78 (m, 2H) 3.36-3.42(m, 1H) 4.30 (t, J=12.8 Hz, 2H) 4.51 (s, 2H) 7.21-7.38 (m, 6H) 7.48 (d, J=8.0 Hz, 1H) 7.86 (d, J=7.6 Hz, 1H) 7.94 (s, 1H)

EXAMPLE 19

The Synthesis of 4-[4-(benzyloxy)piperidino]butyl 3-fluorobenzoate

To 26 mL of chloroform was added 4-[4-(benzyloxy)piperidino]-1-butanol, which was obtained from step 2 of example 12 (0.7 g), 3-fluorobenzoic acid (0.56 g), 4-dimethylaminopyridine (0.97 g), 1-[3-(dimethylamino)propyl]-3-ethylcarboimide hydrochloric acid (0.56 g). The resulting mixture was allowed to react at room temperature for 4 hrs. before adding water to end the reaction. The resulting solution was acidified with 1N hydrochloric acid, and extracted by using chloroform. An organic solution layer was washed with 1N sodium hydroxide, dehydrated over magnesium sulfate, filtered, and concentrated under reduced pressure. The column chromatography was performed thereon, thereby obtaining crude yellowish liquid product (0.49 g, 48% yield) of the title.

$^1$H-NMR(CDCl$_3$): 1.64-1.79 (m, 6H) 1.89-1.94 (m, 2H) 2.08-2.17 (m, 2H) 2.35 (t, J=15.2 Hz, 2H) 2.73-2.84 (m, 2H) 3.39-3.44 (m, 1H) 4.31 (t, J=12.8 Hz, 2H) 4.51 (s, 2H) 7.24-7.66 (m, 7H) 7.80 (d, J=2.8 Hz, 1H) 7.79 (d, J=3.2 Hz, 1H)

EXAMPLE 20

The Synthesis of 4-[4-(benzyloxy)piperidino]butyl N-(4-chlorophenyl)carbamate

To 26 mL of acetonitrile was added 4-[4-(benzyloxy)piperidino]-1-butanol, which was obtained from step 2 of example 12 (0.7 g), 4-chlorophenyl isocyanate (0.42 g). The mixture was refluxed for 4 hrs. The resulting mixture was cooled, and concentrated under reduced pressure. The resultant mixture was then extracted by using water and chloroform. An organic solution layer was dehydrated over magnesium sulfate, filtered, and concentrated under reduced pressure. The column chromatography was performed thereon, thereby obtaining crude yellowish liquid product (0.67 g, 61% yield) of the title.

$^1$H-NMR(CDCl$_3$): 1.53-1.69 (m, 6H) 1.89-1.99 (m, 2H) 2.08-2.16 (m, 2H) 2.32 (t, J=15.2 Hz, 2H) 2.68-2.74 (m, 2H) 3.38-3.43 (m, 1H) 4.14 (t, J=12.8 Hz, 2H) 4.51 (s, 2H) 6.67 (s, 1H) 7.21-7.32 (m, 9H)

EXAMPLE 21

The Synthesis of 4-[4-(benzyloxy)piperidino]butyl N-(4-fluorophenyl)carbamate

To 37 mL of acetonitrile was added 4-[4-(benzyloxy)piperidino]-1-butanol, which was obtained from step 2 of example 12 (0.99 g), 4-fluorophenyl isocyanate (0.49 mL). The mixture was refluxed for 5 hrs. The reaction mixture was cooled, and concentrated under reduced pressure. The resultant mixture was then extracted by using water and chloroform. An organic solution layer was dehydrated over magnesium sulfate, filtered, and concentrated under reduced pressure. The column chromatography was performed thereon, thereby obtaining crude yellowish liquid product (0.72 g, 48% yield) of the title.

$^1$H-NMR(CDCl$_3$): 1.59-1.71 (m, 6H) 1.88-1.94 (m, 2H) 2.12-2.18 (m, 2H) 2.36 (t, J=14.8 Hz, 2H) 2.78-88 (m, 2H) 3.42-3.48 (m, 1H) 4.18 (t, J=12.6 Hz, 2H) 4.56 (s, 2H) 6.78 (s, 1H) 7.02 (t, J=8.6 Hz, 2H) 7.28-7.36 (m, 7H)

Experiment for Measuring Acetylcholinesterase Inhibition Effect

1. Reagents

The compounds used for measuring acetylcholinesterase (AChE) activity such as acetylcholinesterase (Type V-S: from electric eel), acetylcholine iodide, 5,5-dithio-bis(2-nitro benzoic acid), and neostigmine bromide, were products of Sigma Chemical Co., U.S.A., and high purity reagents were selected for other reagents.

2. Apparatus and Equipment

SmartSpec3000, an UV spectrometer, was manufactured by BioRad Company; Mettler AB204S, chemical balance, was manufactured by Toledo company; pH meter 360 was manufactured by Beckman Company; and other apparatus such as ice maker, water bath, freezer were standard products.

3. Measurement of Acetylcholinesterase Activity

Modified Ellman's method for measuring enzyme activity was used to meet with the measurement of acetylcholinesterase activity. The enzyme was separated into certain amount, and kept under 80° C. below zero. The final concentration of the enzyme used in the experiment was 0.03 unit concentration. 1000 μM of acetylcholine iodide dissolved in 0.1 M sodium phosphate buffer (pH 8.0) was used for substrate. As for dye reagent, 5,5-dithio-bis-(2-nitrobenzoic acid) (39.6 mg) and sodium bicarbonate(15 mg) dissolved in 10 mL sodium phosphate buffer (0.1M, pH 7.0) was used.

The procedure for the enzyme reaction was as follows. After adding 200 μl DTNB and 100 μl enzyme (0.03 U) to 2 mL sodium phosphate buffer (pH 8.0), the resulting mixture was pre-heated at 37° C. for 10 minutes. To the resulting mixture 200 μl substrate was added, and allowed to react for 3 minutes. The spectrometer of finished reaction was measured at 412 nm wave. $IC_{50}$ value connected to activity inhibition was measured by quantal-dose response. The results are summarized in Table 1a and Table 1b.

Experiment for Measuring Inhibition of β-amyloid Aggregation

1. Reagents

As the materials used for measuring β-amyloid aggregation, β-amyloid (1-42) was a product of American Peptide Co., U.S.A.; and thioflavin T, phosphate buffered saline tablets, and dimethyl sulfoxide (DMSO, 99.5%) were products of Sigma Chemical Co., U.S.A., and high purity reagents were selected for other reagents.

2. Apparatus and Equipments

RF-5300PC, a fluorescent spectrometer, was manufactured by Shimadzu Corp.; Mettler AB204S, chemical balance, was manufactured by Toledo company; pH meter 360 was manufactured by Beckman Company; and other apparatus such as ice maker, water bath, freezer were standard products.

3. Experiment for Measuring Inhibition of β-amyloid (1-42) Aggregation

Fluorescent analysis was used in measuring β-amyloid aggregation. This peptide compound was kept in the deep freezer (−80° C.), and the final concentration used in the mesurement was 5 μM. Compounds that need to be analyzed were dissolved in 99.5% DMSO, and fluorescent substance was prepared by dissolving thioflavin T (5 μM) in 0.01 M sodium phosphate buffer.

The procedure for aggregation reaction was as follows. To 0.01 M sodium phosphate buffer (92.5 μl) was added fixed concentration of a compound, for measuring purpose, (5 μl) and 5 μM β-amyloid 1-42 (2.5 μl). The resulting mixture was kept at 37° C. for 26 hours to aggregate. 5 μM tioflavin T (2000 μl) was added thereto, and then fluorescent strength was measured with fluorescent spectrometer. The wavelength of fluorescent spectrometer was set at Ex=446 nm (slit width=5 nm), Em=490 nm (slit width=10 nm), and $IC_{50}$ value connected to aggregation inhibition was measured by quantal-dose response. The results are summarized in Table 1a.

As shown in Table 1a, the piperidine derivatives of Formula 3 synthesized as Example 2, wherein R is chlorobenzyl group and R' is benzhydryl group, are used in the lowest concentration (0.3 μM) to inhibit 50% of enzyme activity. Thus, they are useful as a pharmaceutical composition for treating Alzheimer's disease. Likewise, the piperidine derivatives synthesized as Example 6, wherein R is tert-butyl group and R' is benzhydryl group, are used in the lowest concentration to inhibit β-amyloid aggregation. In general, R' substituted with benzhydryl group, rather than benzyl, was favorable to inhibition of acetylcholinesterase and β-amyloid.

TABLE 1a

| Example | Chemical Structure | AChE Inhibition ($IC_{50}$) | β-Amyloid Aggregation Inhibition ($IC_{50}$) |
|---|---|---|---|
| 1 | (diphenylmethyl-O-piperidine-N-(CH₂)₄-O-C(=O)-C₆H₄-NO₂) | 7.2 μM | 53.14 μM |

TABLE 1a-continued

| Example | Chemical Structure | AChE Inhibition (IC$_{50}$) | β-Amyloid Aggregation Inhibition (IC$_{50}$) |
|---|---|---|---|
| 2 | Ph$_2$CH-O-(piperidine)-N-(CH$_2$)$_4$-O-C(=O)-C$_6$H$_4$-Cl (para) | 0.3 μM | 28.21 μM |
| 3 | Ph$_2$CH-O-(piperidine)-N-(CH$_2$)$_4$-O-C(=O)-C$_6$H$_4$-F (para) | 0.84 μM | 36.33 μM |
| 4 | Ph$_2$CH-O-(piperidine)-N-(CH$_2$)$_4$-O-C(=O)-C$_6$H$_5$ | 1.3 μM | 40.33 μM |
| 5 | Ph$_2$CH-O-(piperidine)-N-(CH$_2$)$_4$-O-C(=O)-C$_6$H$_4$-iPr (para) | 3.89 μM | 76.86 μM |
| 6 | Ph$_2$CH-O-(piperidine)-N-(CH$_2$)$_4$-O-C(=O)-C$_6$H$_4$-tBu (para) | 2.41 μM | 20.02 μM |
| 7 | Ph$_2$CH-O-(piperidine)-N-(CH$_2$)$_4$-O-C(=O)-C$_6$H$_4$-Cl (meta) | 3.39 μM | 91.96 μM |

TABLE 1a-continued

| Example | Chemical Structure | AChE Inhibition (IC$_{50}$) | β-Amyloid Aggregation Inhibition (IC$_{50}$) |
|---|---|---|---|
| 8 |  | 70.7 μM | 33.72 μM |
| 9 |  | 2.45 μM | 37.32 μM |
| 10 |  | 2.45 μM | 113.64 μM |
| 11 |  | >150 μM | 61.15 μM |

TABLE 1b

| Example | Chemical Structure | AChE Inhibition (IC$_{50}$) |
|---|---|---|
| 12 |  | >100 μM |
| 13 |  | >100 μM |
| 14 |  | >100 μM |

TABLE 1b-continued

| Example | Chemical Structure | AChE Inhibition (IC$_{50}$) |
|---|---|---|
| 15 | | >100 μM |
| 16 | | 14.78 μM |
| 17 | | 12.20 μM |
| 18 | | >100 μM |
| 19 | | >100 μM |
| 20 | | >100 μM |
| 21 | | >100 μM |

Acute Toxicity Test

In order for a compound to be comprised in the pharmaceutical composition for treating Alzheimer's disease, it must be nontoxic. The representative compounds synthesized by Example 2 (the best substance for inhibiting acetylcholinesterase) and by Example 6 (the best substance for inhibiting β-amyloid aggregation) were put through an acute toxicity test on animals. This test followed the protocol of Korea Food & Drug Administration. Several groups of ICR mice (male, weight 30±3 g), wherein one group comprises 4 mice, were intraperitoneally injected at once with the above. compound according to the concentration ranging from 50 mg/kg to 500 mg/kg, and the death rate and weight charge was observed for 10 days. The compounds used for the test were diluted with wheat germ oil. Consequently, there were no death in both groups that were injected with compounds from Example 2 and Example 6. Although some weight loss occurred on the first day of injection for groups with 500 mg/kg injection (6.96%) of the compound from Example 2 and 200 mg/kg injection (6.31%) of the compound from Example 6, the weight consistently increased from second day on. Furthermore, there were no problems in the motility of the animals.

Through the experiment, prediction can be made that the fatal dose of the compounds to be much higher in concentration than 500 mg/kg, which prove that these substances are very safe to use. The results are summarized in Table 2 (the compounds of Example 2) and Table 3 (the compounds of Example 6).

TABLE 2

Toxicity Experiment on the Compound Synthesized in Example 2

| Dosage (mg/kg) | days | | | | |
|---|---|---|---|---|---|
| | 0 | 1 | 2 | 6 | 10 |
| 500 | 28.8 | 26.8 | 28.0 | 31.3 | 34.3 |
| Weight Change (%) | | −6.96 | −2.61 | 8.7 | 19.13 |
| 200 | 27.5 | 26.8 | 27.3 | 3.03 | 33.3 |
| Weight Change (%) | | −2.73 | −0.91 | 10 | 20.91 |
| 50 | 27.3 | 27.3 | 27.5 | 29.8 | 32.8 |
| Weight Change (%) | | 0 | 0.92 | 9.17 | 20.18 |
| Control | 27.0 | 26.5 | 27.5 | 29.5 | 32.5 |
| Weight Change (%) | | −1.85 | 1.85 | 9.26 | 20.37 |

TABLE 3

| Toxicity Experiment on the Compound Synthesized in Example 6 | | | | | |
|---|---|---|---|---|---|
| Dosage | days | | | | |
| (mg/kg) | 0 | 1 | 2 | 6 | 10 |
| 500 | 27.0 | 25.5 | 26.3 | 28.8 | 31.8 |
| Weight Change (%) | | −5.56 | −2.78 | 6.48 | 17.59 |
| 200 | 27.8 | 26.0 | 28.3 | 31.0 | 33.8 |
| Weight Change (%) | | −6.31 | 1.8 | 11.71 | 21.62 |
| 50 | 27.0 | 26.0 | 27.0 | 29.3 | 32.3 |
| Weight Change (%) | | −3.70 | 0.00 | 8.33 | 19.44 |
| Control | 27.0 | 26.5 | 27.5 | 29.5 | 32.5 |
| Weight Change (%) | | −1.85 | 1.85 | 9.26 | 20.37 |

The compound of the present application have the structure of piperidine ring having butylcarboxylate functional group, and benzyloxy or benzhydryl functional group. This compound can be a great use as a therapeutic substance by designing and synthesizing in consideration to the distance in reaction site and reactivity of butyl carboxylate group and benzyloxy or benzhydryl group to the parent structure of piperidine. Furthermore, when the electronic donating group and electron withdrawing group were introduced as substitutes of piperidine, the reactivity of the compound showed excellent inhibiting effect on acetylcholinesterase and β-amyloid protein aggregation. Finally, the compounds showed no toxicity on mouse even with 500 mg/kg injection when acute toxicity test was done

INDUSTRIAL AVAILABILITY OF THE INVENTION

As we have described in the above, the present invention can be a great use as a therapeutic substance for Alzheimer's disease due to its excellency in inhibiting acetylcholinesterase and aggregation of β-amyloid protein that relates to causing the disease.

What is claimed is:

1. A piperidine derivative represented by Formula 3:

<Formula 3> wherein R' is benzyl or benzhydryl

R is (i) linear or branched $C_1$-$C_6$ alkyl, (ii)

or (iii) —$NHR_2$;
$R_1$ is —H, —OH, halogen, —$NO_2$, —$NH_2$, linear or branched $C_1$-$C_6$ alkyl;
$X_1$ is C;
$X_2$, $X_3$, $X_4$, $X_5$, and $X_6$ individually are CH or N; and
$R_2$ is H or

2. The piperidine derivative according to claim 1, wherein R is selected from the group consisting of following moieties:

(i) —$CH_3$, —$(CH_2)_n CH_3$ (wherein n is an integer raging from 2 to 5),

-continued

-continued

<Formula 5>

<Formula 6>

<Formula 7>

3. The piperidine derivative according to claim 1, wherein the piperidine derivative is selected from the group consisting of:
   4-[4-(benzhydryloxy)piperidino]butyl-4-nitrobenzoate;
   4-[4-(benzhyryloxy)piperidino]butyl-4-chlorobenzoate;
   4-[4-(benzhydryloxy)piperidino]butyl-4-fluorobenzoate;
   4-[4-(benzhydryloxy)piperidino]butyl benzoate;
   4-[4-(benzhydryloxy)piperidino]butyl-4-isopropylbenzoate;
   4-[4-(benzhydryloxy)piperidino]butyl-4-(tertiary-butyl) benzoate;
   4-[4-(benzhydryloxy)piperidino]butyl-3-chlorobenzoate;
   4-[4-(benzhydryloxy)piperidino]butyl-3-fluorobenzoate;
   4-[4-(benzhydryloxy)piperidino]butyl-N-(4-chlorophenyl)carbamate;
   4-[4-(benzhydryloxy)piperidino]butyl-N-(4-fluorophenyl)carbamate;
   4-[4-(benzhydryloxy)piperidino]butyl nicotinate;
   4-[4-(benzyloxy)piperidino]butyl-4-nitrobenzoate;
   4-[4-(benzyloxy)piperidino]butyl-4-chlorobenzoate;
   4-[4-(benzyloxy)piperidino]butyl4-fluorobenzoate;
   4-[4-(benzyloxy)piperidino]butyl benzoate;
   4-[4-(benzyloxy)piperidino]butyl-4-isopropylbenzoate;
   4-[4(benzyloxy)piperidino]butyl-(tertiary-butyl)benzoate;
   4-[4-(benzyloxy)piperidino]butyl-3-chlorobenzoate;
   4-[4-(benzyloxy)piperidino]butyl-3-fluorobenzoate;
   4-[4-(benzyloxy)piperidino]butyl-N-(4-chlorophenyl) carbamate; and
   4-[4-(benzyloxy)piperidino]butyl-N-(4-fluorophenyl)carbamate.

4. A process for preparing the piperidine derivative of claim 1 comprising the steps of:
   (a) reacting a compound of Formula 4 and a compound of Formula 5 to obtain a compound of Formula 6;
   (b) reducing the compound of Formula 6 to obtain a compound of Formula 7;
   (c) reacting the compound of Formula 7 with RCOOH or R—N=C=O to obtain a compound of Formula 3:

<Formula 3>

<Formula 4> wherein, R' is benzyl or benzhydryl

R is (i) linear or branched $C_1$-$C_6$ alkyl, (ii)

or (iii) —$NHR_2$;

$R_1$ is —H, —OH, halogen, —$NO_2$, —$NH_2$, linear or branched $C_1$-$C_6$ alkyl;

$X_1$ is C;

$X_2$, $X_3$, $X_4$, $X_5$, and $X_6$ individually are CH or N; and

$R_2$ is H or

R" is $C_1$-$C_4$ alkyl; and

X is a halogen element.

5. The process according to claim 4, comprising the steps represented by the following Reaction Scheme 2:

<Reaction Scheme 2>

6. A pharmaceutical composition for treating Alzheimer's disease, comprising an effective amount of the piperidine derivative described in claim 1 or its pharmaceutically acceptable salts.

7. The pharmaceutical composition according to claim 6 further comprising a pharmaceutically acceptable carrier.

8. The pharmaceutical composition according to claim 6, wherein the composition is used for an oral administration further comprising:
   (i) a capsule excipient;
   (ii) a tablet excipient;
   (iii) an additive selected from the group consisting of: starch, crystallized cellulose, hydroxyproplymethyl cellulose, polyethylene glycol, lactose, polyvinyl pyrrolidone, and glyceryl behanate
   (iv) a diluent;
   (v) a wet binder;
   (vi) a lubricant;
   (vii) a fluidizing agent; or
   (viii) an adhesion inhibitor.

9. The pharmaceutical composition according to claim 6, wherein the composition is used for an injection further comprising:
   (i) a solvent;
   (ii) a diluent; or
   (iii) an antiseptic.

* * * * *